United States Patent [19]
Dobson

[11] Patent Number: 5,876,783
[45] Date of Patent: Mar. 2, 1999

[54] RADIOPAQUE MEDICAL DEVICES

[75] Inventor: Paul J. Dobson, Hingham, Mass.

[73] Assignee: The MicroSpring Company, Inc., Norwell, Mass.

[21] Appl. No.: 965,103

[22] Filed: Nov. 6, 1997

Related U.S. Application Data

[62] Division of Ser. No. 492,921, Jun. 20, 1995, Pat. No. 5,724,989.

[51] Int. Cl.[6] .......................... C23C 14/06; C23C 14/18; B21C 47/00; B05D 3/12
[52] U.S. Cl. ..................... 427/2.12; 427/178; 427/160; 427/528; 427/531
[58] Field of Search .................... 427/2.28, 160, 427/528, 531, 178, 2.12, 2.31; 128/772

[56] References Cited

U.S. PATENT DOCUMENTS

| | | | |
|---|---|---|---|
| 3,916,877 | 11/1975 | Beckman | 128/2.05 R |
| 4,592,372 | 6/1986 | Beranek | 128/786 |
| 4,807,596 | 2/1989 | Hochberger et al. | 128/4 |
| 4,939,041 | 7/1990 | Kabacoff et al. | 428/607 |
| 5,107,852 | 4/1992 | Davidson et al. | 128/772 |
| 5,144,959 | 9/1992 | Gambale et al. | 128/772 |
| 5,253,653 | 10/1993 | Daigle et al. | 128/772 |
| 5,313,943 | 5/1994 | Houser et al. | 128/642 |
| 5,345,945 | 9/1994 | Hodgson et al. | 128/772 |
| 5,437,288 | 8/1995 | Schwartz et al. | 128/772 |
| 5,460,187 | 10/1995 | Daigle | 128/772 |
| 5,599,492 | 2/1997 | Engelson | 264/167 |
| 5,630,840 | 5/1997 | Mayer | 623/1 |
| 5,666,969 | 9/1997 | Urick et al. | 128/772 |

*Primary Examiner*—Diana Dudash
*Attorney, Agent, or Firm*—Hale & Dorr LLP

[57] ABSTRACT

A method and apparatus for producing a guide wire including a core wire a distal portion of which is surrounded by a helically wound spring. The coils forming the distal portion of the spring include a annular layer of radiopaque material, e.g., gold, ion deposited onto the stainless steel wire of the spring.

13 Claims, 1 Drawing Sheet

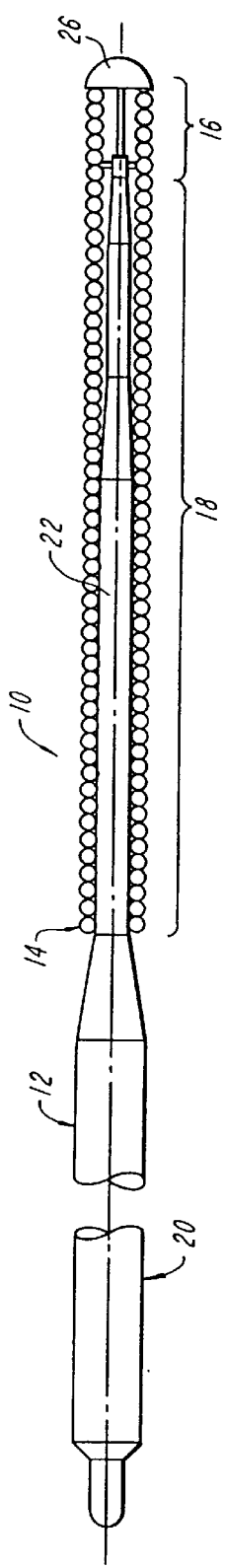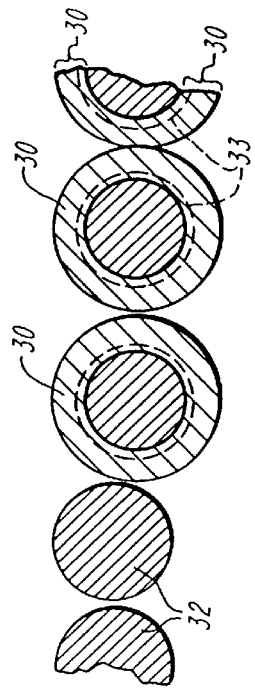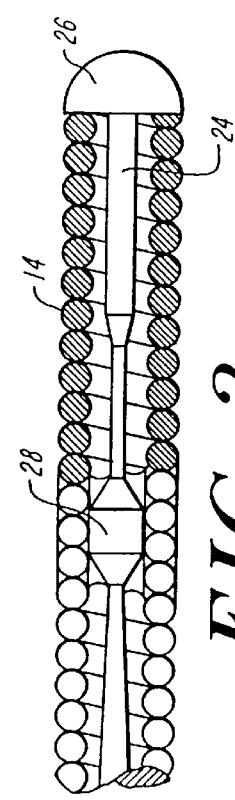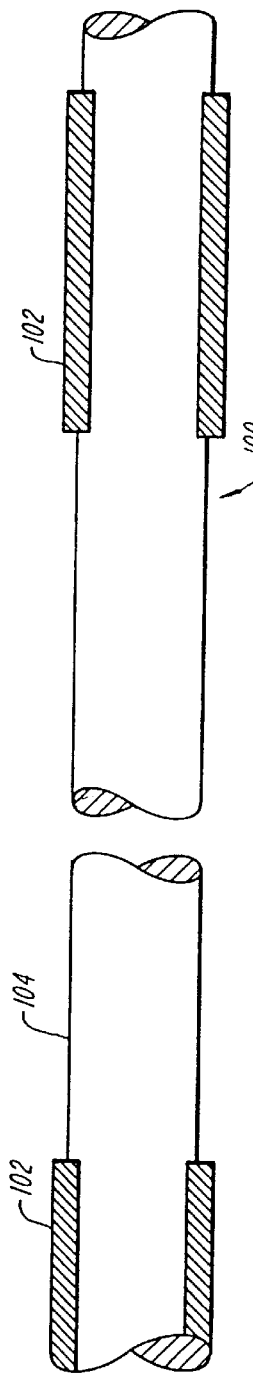
FIG. 1
FIG. 2
FIG. 3
FIG. 4

RADIOPAQUE MEDICAL DEVICES

This application is a division of application Ser. No. 08/492,921, filed Jun. 20, 1995, now U.S. Pat. No. 5,724,989.

FIELD OF INVENTION

This invention relates to radiopaque medical devices and, more particularly, to guide wires used to introduce catheters into human cardiovascular systems and having a radiopaque distal end portion.

BACKGROUND OF INVENTION

There are in the art a number of flexible guide wires used in medical applications. Exemplary such devices are shown in U.S. Pat. Nos. 3,545,390, 4,538,622, 4,619,274, 5,053,404, and 5,267,574, and in U.S. application Ser. No. 08/069,050 filed May 28, 1993, now U.S. Pat. No 5,606,979 and owned by the assignee of the present application, all of which are here incorporated by reference. Some such devices, including those shown in U.S. Pat. Nos. 4,538,622 and 5,052,404, include a flexible main spring of stainless steel having a short radiopaque (e.g., platinum, gold, tantalum, tungsten, iridium, rhenium) spring joined to its distal end. In others, such as those shown in U.S. Pat. Nos. 3,545,390 and 5,267,574, the entire spring is made of a material (e.g., platinum or a platinum/tungsten alloy, having a relative high radiopacity. Whether the spring is one-piece or two-piece, a central core, which also may be stainless steel, typically extends coaxially within the entire length of the spring and is connected, e.g., by brazing, to both the distal and proximal ends of the spring. When a two-piece spring is employed, the adjacent ends of the two pieces of the spring are generally brazed both to each other and to the central core of the guide wire assembly.

Medical devices in which an entire spring is made of a radiopaque material such as tungsten are expensive, and the material may have less desirable characteristics than does a material such as stainless steel. Making only a portion, e.g., the distal end portion, of the spring of a radiopaque material somewhat reduces material costs, but requires two or more springs rather than one, along with the additional manufacturing costs and procedures that are required to insure a secure construction.

There have been attempts to provide guide wires having a two-piece construction in which a single stainless steel coil extends all the way to the tip, but these attempts have proved to be somewhat unsatisfactory. Neither the stainless steel itself, nor a layer of gold or the like plated onto the coil, has been sufficiently radiopaque.

There remains a need for a less-expensive spring device that is sufficiently radiopaque, and particularly for a guide wire having a radiopaque distal end.

SUMMARY OF THE INVENTION

The present invention provides medical device including a helical coil spring in which a length of the wire forming at least some of the spring coils includes an annular layer of radiopaque material surrounding the central cylindrical portion of the spring wire, the annular layer of radiopaque material being deposited on the length of wire that will form the coils before the spring is wound. In preferred embodiments, the medical device is a guide wire assembly in which a single helical coil extends proximally from the distal end, the length of wire forming the coils adjacent the distal end includes the annular radiopaque layer, the radiopaque material is placed on the length of wire and the entire helical coil spring wound before the wound spring is placed in position around the central core of the guide wire assembly. Preferred embodiments also feature springs in which the radiopaque material is gold; and the gold is deposited circumferentially onto the length of the wire using an ion-beam procedure (such as those known as ion-beam implantation or ion-beam assisted deposition, see, e.g., U.S. Pat. Nos. 5,236,509, 4,743,308 and 4,526,673 which are here incorporated by reference) such that the ion-implantation/ion-beam-assisted-deposition increases the diameter of the base wire by not more than about 0.002 in. (or about 0.05 mm.), and preferably by about 0.0005 to 0.001 in. (or about 0.00125 to 0.0025 mm.).

DESCRIPTION OF DRAWINGS

FIG. 1 is a sectional view of a guide wire assembly constructed in accord with the present invention.

FIG. 2 is an enlarged sectional view of the tip portion of the guide wire assembly of FIG. 1.

FIG. 3 is a greatly enlarged sectional view of the coil in the distal tip portion of the guide wire assembly of FIG. 1.

FIG. 4 is a schematic view of the wire used in the coil of the guide wire assembly of FIG. 1.

DESCRIPTION OF PREFERRED EMBODIMENTS

Reference is now made to FIGS. 1–3 which illustrate a guide wire assembly generally designated 10. It will be appreciated that, largely because the guide wire is about 6' long and only about 0.014 in. in diameter, the longitudinal and transverse scales of the drawings are very different.

As shown, guide wire assembly 10 includes a core wire 12, a portion of which is surrounded by a coaxial, helically wound spring 14. A distal tip portion 16 of the guide wire assembly is about 2.7 centimeters (a little over 1 inch) long. An intermediate portion 18 is about 25 centimeters (about 10 inches) long and extends from the proximal end of tip portion 16; and a main guide wire portion 20 extends some 140 centimeters (about 4 ½ feet) proximally from the proximal end of the intermediate portion 18. Spring 14 extends from the distal end of the distal tip portion 16 to the proximal end of the intermediate portion 18, and both the proximal and distal end portions of spring 14 are welded or brazed to core wire 12.

The solid core wire 12 includes an approximately constant diameter portion (about 4 ½ feet long and 0.0013 in. in diameter) forming main guide wire portion 20 of assembly 18, and a distal portion 22 of reduced diameter. Distal portion 22 extends, coaxially within spring 14, through the length of intermediate portion 18 to adjacent the distal end of tip portion 16. The distal end of distal portion 22 of core wire 12 terminates in a flat portion 24 that is secured (typically brazed or welded) to an essentially hemispherical tip 26.

The diameter of the stainless steel wire forming the coils of spring 14 is about 0.0025 in. The coils of spring 14 are typically formed by wrapping the stainless steel wire on a constant diameter mandrel so that the inner diameter of the spring coils is constant, and so that the spring has an overall outer diameter of about 0.013 (and a maximum diameter of 0.014 in) throughout most of its length. As discussed below, the overall diameter of the wire forming the spring coils in the distal portion of guide wire 10 is slightly (e.g., about 0.00008 to 0.002 in. and typically about 0.0005 to 0.001 in.) greater than that of coils in the remaining portion of the spring, because in the distal portion the stainless steel wire has been increased by circumferentially deposited radiopaque material.

It will be evident that, alternatively, the wire forming the coils may be wrapped on a tapered mandrel so that the overall outer diameter of the spring coil is constant, or so that the diameter of the center of the stainless steel wire of the coils is constant. In the latter event, the portion of the spring 14 in tip portion 16 will have an overall outer diameter that is slightly (by an amount equal to the difference in diameter of the coated coil wire caused by the radiopaque material deposited on the stainless steel) greater than that of the remaining, and major, portion of the spring in which there is no such radiopaque layer.

As seen most clearly in FIG. 2, core wire 12 includes an annular ring 28, about 0.4 cm (about 0.015 inches in axial length) and, typically, about 0.016 cm. (about 0.0076 in.), located approximately 2.7 cm (a little more than 1 inch) from the distal end of the core wire. The annular outer surface of ring 28 is brazed to the surrounding portion of spring 14, and the exact diameter of the ring 28 is selected so that the overall diameter of the portion of spring 14 brazed to it will be about 0.0013 in. The portion of spring 14 surrounding and brazed to ring 28 is helically wound at about 60 coils per inch (about 24 coils per centimeter); the portion of spring 14 between ring 28 and tip 26 is wound at approximately 280 coils per inch (about 110 coils per centimeter); and the portion of sprint 14 proximal of ring 28 is wound at about 334 coils per inch (about 131 coils per centimeter).

According to the present invention, the wire forming the coils in the distal approximately 2.5 cm. (about 1 inch) of spring 14 includes a annular, circumferentially surrounding layer 30 of radiopaque material having an outer diameter not more than about 0.002 in. (about 0.05 mm.) greater than that of the stainless steel central portion 32 of spring 14 on which the radiopaque material is deposited. In FIG. 2, the spring coils which include layer 30 are cross-hatched; FIG. 3, which is greatly enlarged, shows both annular layer 30 and the central portion 32 of the stainless steel wire that the layer 30 circumferentially surrounds. In the preferred embodiment the diameter of layer 32 is about 0.0005 to 0.001 in. (about 0.00125 to 0.0025 mm.) more than that of the stainless steel central portion 32.

As discussed above, it will be appreciated that layer 30 increases the overall outer diameter of spring 14 in the tip portion 16 of guide wire 10 by an amount substantially equal to that by which the layer increases the overall diameter of the wire forming the spring coils in the tip region. However, because the layer of radiopaque material is annular and circumferentially surrounds the wire forming the coils, the radiopacity of the spring in the tip portion 16 is much more than it would be if a layer of radiopaque material of the same thickness was simply deposited on the spring after it had been wound.

According to the preferred practice of the present invention, an ion beam process is used to deposit the layer of radiopaque material onto the stainless steel wire that is then wound into spring 14. In an ion beam deposition process, atoms of material being deposited, together with ions from the ion beam, are typically both driven into and deposited on the surface of the workpiece, e.g., the stainless steel wire of spring 14. See, e.g., aforementioned U.S. Pat. Nos. 4,743,308 and 5,236,509. Thus, and as shown in FIG. 3, the "layer" 30 extends below the surface 33 of the stainless steel wire onto which the material forming the layer is ion-deposited, and the effective overall thickness of the "layer" 30 formed by the ion beam process is greater than the amount by which the deposited material increases the radius of the stainless steel of central portion 32. The use of an ion beam deposition process accordingly results in a degree of radiopacity that is considerably greater than is obtained by plating a annular layer of the same material onto the base wire at a thickness that would produce the same amount of increase in the base wire's radius or diameter.

In the preferred embodiment, layer 30 is gold iondeposited (e.g., by Spire Corporation of Bedford, Mass. using the procedure identified by the trademark "Spi-Sight") onto the stainless steel wire of spring 14 so as to increase the overall radius of the stainless steel by about 0.00025 in. to 0.0005 in. (and the diameter of both the stainless steel wire of the spring 14 and of the wound spring itself by about 0.0005 in. to about 0.001 in.). The effective thickness of layer 30, however, is considerably greater than 0.00025 in., and layer 30 provides a radiopacity that otherwise would be extremely difficult to achieve without increasing the overall diameter of spring 14 to more than the maximum permissible 0.014 in.

FIG. 4 illustrates a continuous length of the wire 100 used to make a plurality of springs 14, before it has been helically wound. As shown, circumferential layers 102 of gold, each about 40 inches long and about 0.00025 inches in radial thickness, are ion-deposited onto axially spaced portions of the about 0.0025 inch. diameter 304 stainless steel wire. The approximately 280 inches (about 710 cm) of wire 100 between each adjacent pair of gold layers 102, designated 104, is bare.

About 11 inches of straight wire is required to form the radiopaque coils in the distal portion of a spring 14, i.e., the approximately 2.7 cm (a little over 1 inch) long portion extending from hemispherical tip 26 to a point just distal of annular ring 28. Another approximately 135–140 inches of straight wire are needed to form the bare coils of spring 14 that extend proximally about another 25 centimeters (about 10 inches) from the proximal end of the gold-layered distal portion coils.

It will thus be noted that the lengths of each gold layer 102 and bare portion 104 are about twice the length needed to form a helically wound spring wire 14. Thus, in forming a wire 14 for a guide wire assembly 10, the wire 100 is first helically wrapped into coils of the desired diameter and spacing, and the bare portions 14 and gold layer portions 102 of the wrapped coil are then cut approximately midway their respective lengths. A cut length may then be slipped over the core wire 12 (on the distal end of which hemispherical tip 26 has already been welded), and brazed into place. Short lengths of "scrap" may be removed at the distal and proximal ends of the helical coil 14 in the course of assembly and brazing.

In other embodiments, dense radiopaque materials other than gold (e.g., platinum, tantalum, tungsten, iridium, rhenium, or an alloy of two or more such materials) may be ion implanted to form the desired increased radiopacity annular layers on the stainless steel spring wire, and the springs may be used in medical devices other that guide wires. In some circumstances it may also be possible to provide a layer with the desired radiopacity using a procedure other than ion implantation.

These and other embodiments will be within the scope of the following claims.

What is claimed is:

1. In the method of making a guide wire assembly including a helically wound spring coaxially surrounding a central core and extending distally from the distal tip of said guide wire, that improvement including the steps of:

providing a length of wire for making said spring;

depositing an annular layer of radiopaque material on an axially-extending portion of said length of wire;

winding said length of wire into a helically wound spring, one portion of said spring comprising coils formed from said axially-extending portion including said annular layer and another portion of said spring comprising coils formed from a portion of said wire that does not include said annular layer;

positioning said spring relative to a said central core such that said one portion of said spring extends from the distal tip of said guide wire assembly to a point proximal of said distal tip.

2. The method of claim 1 wherein said radiopaque material is selected from the group consisting of gold, platinum, tantalum, tungsten, iridium, rhenium, and two or more thereof.

3. The method of claim 2 wherein said depositing comprises ion-depositing said material onto said axially-extending portion.

4. The method of claim 1 wherein said forming includes ion-depositing gold onto said axially-extending portion.

5. The method of claim 1 wherein said forming includes ion-depositing said radiopaque material such that said layer has an outer diameter not more than about 0.0004 inches greater than that of said core wire onto which the said radiopaque material forming said layer is deposited.

6. The method of claim 1 wherein said outer diameter is not more than about 0.002 inches greater than that of said core wire, and said layer comprises ion-deposited gold.

7. The method of claim 6 wherein said outer diameter is not more than about 0.001 inches greater than that of said core wire.

8. The method of claim 1 wherein said core wire includes an annular ring adjacent the distal end of said distal portion of said core wire, and including the step of brazing said one portion of said spring to said annular ring.

9. The method of claim 1 wherein said tip portion of said guide wire includes a rounded tip attached to the distal end of said core and the distal end of said helical spring.

10. In the method of making a medical device including a helically wound spring, that improvement including the steps of:

providing a length of wire for making said spring;

ion-depositing an annular layer of radiopaque material on an axially-extending portion of said length of wire;

winding said length of wire into said helically wound spring, one portion of said spring comprising coils formed from said axially-extending portion including said annular layer and another portion of said spring comprising coils formed from a portion of said wire that does not include said annular layer.

11. The method of claim 10 wherein said radiopaque material is selected from the group consisting of gold, platinum, tantalum, tungsten, iridium, rhenium, and two or more thereof.

12. The method of claim 10 wherein said forming includes ion-depositing said radiopaque material such that said layer has an outer diameter not more than about 0.002 inches greater than that of said wire onto which the said radiopaque material forming said layer is deposited.

13. The method of claim 12 wherein said outer diameter is not more than about 0.001 inches greater than that of said core wire, and said layer comprising ion-deposited gold.

* * * * *